(12) United States Patent
Ballantyne et al.

(10) Patent No.: US 7,270,983 B1
(45) Date of Patent: Sep. 18, 2007

(54) MESSENGER RNA PROFILING: BODY FLUID IDENTIFICATION USING MULTIPLEX REVERSE TRANSCRIPTION-POLYMERASE CHAIN REACTION (RT-PCR)

(75) Inventors: Jack Ballantyne, Chuluota, FL (US); Jane Juusola, Winter Springs, FL (US)

(73) Assignee: Research Foundation of The University of Central Florida, Inc., Orlando, FL (US)

( * ) Notice: Subject to any disclaimer, the term of this patent is extended or adjusted under 35 U.S.C. 154(b) by 0 days.

(21) Appl. No.: 11/050,538

(22) Filed: Feb. 3, 2005

Related U.S. Application Data

(60) Provisional application No. 60/545,792, filed on Feb. 19, 2004.

(51) Int. Cl.
*C12P 19/34* (2006.01)
*C12Q 1/68* (2006.01)

(52) U.S. Cl. .................. 435/91.2; 435/6; 536/25.41

(58) Field of Classification Search .............. 435/91.2
See application file for complete search history.

(56) References Cited

OTHER PUBLICATIONS

Bauer, et al, "Evaluation of mRNA markers for the Identification of Menstrual Blood," Journal of Forensic Sciences, Nov. 2002, vol. 47, No. 6, pp. 1278-1282.*

Absolutely RNA Nanoprep kit: Instruction Manual, Stratagene; http://www.stratagene.com/products/displayProduct.aspx?pid=137.*

Bauer et al, "Protamine mRNA as molecular marker for spermatozoa in semen stains," International Journal of Legal Medicine, 2003, 117, 175-179.*

Gubin, A., et al, Human erythroid porphobilinogen deaminase exists in 2 splice variants, Blood, Feb. 2001, vol. 97, No. 3, pp. 815-817.*

Alberts, Bruce, et al. *Molecular Biology of the Cell*, 4th ed., (2002). Chapter II. Section 7. "The Molecular Genetic Mechanisms That Create Specialized Cell Types." http://www.ncbi.nlm.nih.gov/entrez/query.fegi?cmd=Search&db=books&doptcmdl=GenBo ....

Bauer, M., et al. *International Journal of Legal Medicine*. vol. 117 pp. 175-179. (2003). "Protamine mRNA as Molecular Marker for Spermatozoa in Semen Stains."

Gubin, Alexander, et al. *Blood*. vol. 97. No. 3. (2001). "Human Erythroid Porphobilinogen Deaminase Exists in 2 Splice Variants."

Juusola, Jane, et al. *Forensic Science International*. vol. 135. p. 85-96. (2003). "Messenger RNA profiling: A Prototype Method to Supplant Conventional Methods for Body Fluid Identification."

Steger, Klaus, et al. *Molecular Human Reproduction*. vol. 6. No. 3. pp. 219-225. (2000). "Expression of Protamine -1 and -2 mRNA During Human Spermiogenesis."

* cited by examiner

*Primary Examiner*—Kenneth R. Horlick
*Assistant Examiner*—Molly E. Baughman
(74) *Attorney, Agent, or Firm*—Brian S. Steinberger; Joyce P. Morlin; Law Offices of Brian S. Steinberger, P.A.

(57) ABSTRACT

This invention relates to a body fluids identification method and kit. A parallel, multiplex reverse transcription-polymerase chain reaction (RT-PCR) assay for the definitive identification of body fluids commonly encountered in forensic casework analysis, namely blood, saliva, semen, and vaginal secretions. The methodology is based on gene expression profiling analysis in which the body fluid-specific genes are identified by detecting the presence of appropriate messenger RNA species. Gene-specific primers are labeled with fluorescent dyes, separated and subjected to laser induced fluorescence for identification of body fluid-specific genes present in a sample stain.

9 Claims, 1 Drawing Sheet

| Body Fluid | Gene | Primer Sequences/dyes | Size |
|---|---|---|---|
| Blood | SPTB | 5'- 6-FAM- agg atg gct tgg cct tta at (Seq ID 1)<br>5'- act gcc agc acc ttc atc tt (Seq ID 2) | 247 bp |
| | PBGD | 5'- TET- tgg atc cct gag gag ggc aga ag (Seq ID 3)<br>5'- tct tgt ccc ctg tgg tgg aca tag caa t (Seq ID 4) | 177 bp |
| Saliva | STATH | 5'- 6-FAM- ctt ctg tag tct cat ctt g (Seq ID 5)<br>5'- tgg ttg tgg gta tag tgg ttg ttc (Seq ID 6) | 198 bp |
| | HTN3 | 5'- 6-FAM- gca aag aga cat cat ggg ta (Seq ID 7)<br>5'- gcc agt caa acc tcc ata atc (Seq ID 8) | 134 bp |
| Semen | PRM1 | 5'- HEX- gcc agg tac aga tgc tgt cgc ag (Seq ID 9)<br>5'- tta gtg tct tct aca tct cgg tct (Seq ID 10) | 153 bp |
| | PRM2 | 5'- 6-FAM- gtg agg agc ctg agc gaa cgc (Seq ID 11)<br>5'- tta gtg cct tct gca tgt tct ctt c (Seq ID 12) | 294 bp |
| Vaginal Secretions | HBD-1 | 5'- 6-FAM- ttc ctg aaa tcc tga gtg tt (Seq ID 13)<br>5'- taa cag gtg cct tga att tt (Seq ID 14) | 213 bp |
| | MUC4 | 5'- HEX- gga cca cat ttt atc agg aa (Seq ID 15)<br>5'- tag aga aac agg gca tag ga (Seq ID 16) | 235 bp |

SEQUENCE LISTING

<160> NUMBER OF SEQ ID NOS: 16

<210> SEQ ID NO 1
<211> LENGTH: 20
<212> TYPE: DNA
<213> ORGANISM: Homo sapiens

<400> SEQUENCE: 1
aggatggctt ggcctttaat                                                        20

<210> SEQ ID NO 2
<211> LENGTH: 20
<212> TYPE: DNA
<213> ORGANISM: Homo sapiens

<400> SEQUENCE: 2
actgccagca ccttcatctt                                                        20

<210> SEQ ID NO 3
<211> LENGTH: 23
<212> TYPE: DNA
<213> ORGANISM: Homo sapiens

<400> SEQUENCE: 3
tggatccctg aggagggcag aag                                                    23

<210> SEQ ID NO 4
<211> LENGTH: 28
<212> TYPE: DNA
<213> ORGANISM: Homo sapiens

-continued

```
<400> SEQUENCE: 4
tcttgtcccc tgtggtggac atagcaat                                          28

<210> SEQ ID NO 5
<211> LENGTH: 19
<212> TYPE: DNA
<213> ORGANISM: Homo sapiens

<400> SEQUENCE: 5
cttctgtagt ctcatcttg                                                    19

<210> SEQ ID NO 6
<211> LENGTH: 24
<212> TYPE: DNA
<213> ORGANISM: Homo sapiens

<400> SEQUENCE: 6
tggttgtggg tatagtggtt gttc                                              24

<210> SEQ ID NO 7
<211> LENGTH: 20
<212> TYPE: DNA
<213> ORGANISM: Homo sapiens

<400> SEQUENCE: 7
gcaaagagac atcatgggta                                                   20

<210> SEQ ID NO 8
<211> LENGTH: 21
<212> TYPE: DNA
<213> ORGANISM: Homo sapiens

<400> SEQUENCE: 8
gccagtcaaa cctccataat c                                                 21

<210> SEQ ID NO 9
<211> LENGTH: 23
<212> TYPE: DNA
<213> ORGANISM: Homo sapiens

<400> SEQUENCE: 9
gccaggtaca gatgctgtcg cag                                               23

<210> SEQ ID NO 10
<211> LENGTH: 24
<212> TYPE: DNA
<213> ORGANISM: Homo sapien

<400> SEQUENCE: 10
ttagtgtctt ctacatctcg gtct                                              24

<210> SEQ ID NO 11
<211> LENGTH: 21
<212> TYPE: DNA
<213> ORGANISM: Homo sapien

<400> SEQUENCE: 11
gtgaggagcc tgagcgaacg c                                                 21

<210> SEQ ID NO 12
<211> LENGTH: 25
<212> TYPE: DNA
<213> ORGANISM: Homo sapien
```

```
<400> SEQUENCE: 12
ttagtgcctt ctgcatgttc tcttc                                              25

<210> SEQ ID NO 13
<211> LENGTH: 20
<212> TYPE: DNA
<213> ORGANISM: Homo sapien

<400> SEQUENCE: 13
ttcctgaaat cctgagtgtt                                                    20

<210> SEQ ID NO 14
<211> LENGTH: 20
<212> TYPE: DNA
<213> ORGANISM: Homo sapien

<400> SEQUENCE: 14
taacaggtgc cttgaatttt                                                    20

<210> SEQ ID NO 15
<211> LENGTH: 20
<212> TYPE: DNA
<213> ORGANISM: Homo sapien

<400> SEQUENCE: 15
ggaccacatt ttatcaggaa                                                    20

<210> SEQ ID NO 16
<211> LENGTH: 20
<212> TYPE: DNA
<213> ORGANISM: Homo sapien

<400> SEQUENCE: 16
tagagaaaca gggcatagga                                                    20
```

MESSENGER RNA PROFILING: BODY FLUID IDENTIFICATION USING MULTIPLEX REVERSE TRANSCRIPTION-POLYMERASE CHAIN REACTION (RT-PCR)

This invention claims the benefit of priority from U.S. Provisional Application Ser. No. 60/545,792 filed Feb. 19, 2004.

FIELD OF THE INVENTION

This invention relates to a ribonucleic acid (RNA) based assay system and kit for body fluid identification, and in particular to a novel, multiplex, parallel assay system based on messenger RNA expressed in human tissue, and to a method for using the same.

BACKGROUND AND PRIOR ART

Conventional methods of body fluid identification use a variety of labor-intensive, technologically diverse techniques that are performed in a series, not parallel, manner and are costly in terms of time and consumption of sample. It used to be standard practice to perform biochemical, serological, and immunological tests to identify the body fluid(s) comprising a biological stain. Increasingly, however, classical methods for body fluid identification have no confirmatory technique for some frequently encountered body fluids. For example, there is no definitive test for the presence of saliva or vaginal secretions, and urine identification can be problematic. The need exists for a more reliable, efficient assay system to supplant conventional methods for body fluid identification.

Previous research in the development of a ribonucleic acid (RNA) based assay system for the identification of body fluids, included considerations for the use of protein and messenger RNA (mRNA) since both are expressed in a tissue-type specific manner. However, multiplex analysis of complex protein mixtures, such as those present in body fluid stains, requires further developments in the field of proteomics. Whereas, with messenger RNA (mRNA), the molecular intermediate between genetic DNA and expressed protein is at present, supported by technologies for massively parallel analysis in the field of genomics.

As reported by B. Alberts, et al. *Molecular Biology of the Cell* 3$^{rd}$ ed., Garland Publishing Inc., NY, 1994, a pattern of gene expression is produced that is unique to each cell type and is evinced by the presence as well as the relative abundance of specific mRNAs. Each cell type, such as, blood monocytes, lymphocytes, ejaculated spermatozoa, epithelial cells lining the oral cavity or epidermal cells, has a unique pattern of gene expression.

Specific gene expression patterns for saliva were reported by J. Juusola and J. Ballantyne in February 2002 in a presentation to the American Academy of Forensic Science (AAFS) entitled, "The Development of an RNA Based Assay System for Body Fluid Identification," and in *Forensic Science International*, Vol. 135 (2003) pages 85-96 ("Messenger RNA Profiling: a Prototype Method to Supplant Conventional Methods for Body Fluid Identification"). Semen specific genes were reported by J. Juusola and J. Ballantyne in "The Development of an RNA Based Assay System for Body Fluid Identification," presented to AAFS, February 2002. M. Bauer and D. Patzelt also identified semen specific genes in an article, "Protamine mRNA as Molecular Marker for Spermatozoa in Semen Stains," *International Journal of Legal Medicine* Vol. 117 (2003) pages 175-179.

As more and more tissue-specific genes (mRNAs) are identified for use in the positive identification of body fluids and tissues of forensic importance, there is an increasing need for a device or assay system that provides simultaneous and semi-automatic analysis through a common assay format. The novel, multiplex, parallel assay system of the present invention provides a common assay format and offers many advantages over the conventional analysis procedures for body fluid identification.

SUMMARY OF THE INVENTION

A primary objective of the present invention is to provide facile identification of the tissue components present in a body fluid stain.

A second objective of the present invention is to supplant the battery of serological and biochemical tests currently employed in the forensic serology laboratory.

A third objective of the present invention is to provide a common assay format that provides greater specificity in the identification of body fluids with improved timeliness.

A fourth objective of the present invention is to decrease sample consumption during analysis of stains containing body fluids.

A fifth objective of the present invention is to provide simultaneous and semi-automated analysis through a common assay format.

A sixth objective of the present invention is to provide a multiplex analysis of body fluids in an assay format that is compatible with DNA extraction methodologies.

A seventh objective of the present invention is to provide a kit that can be used to identify the source of at least four body fluids from a human being found in a single stain or a mixed stain.

A preferred method for preparing a multiplex, parallel assay to identify the source of at least four body fluids from a human being includes obtaining a sample stain consisting of a body fluid from a human being, extracting total ribonucleic acid (RNA) from the sample stain, treating the total RNA with an enzyme, initiating a reverse-transcriptase (RT) reaction by treating total RNA with random decamers to produce cDNA, amplifying the cDNA using gene-specific primers, controlling the size of the amplified cDNA to allow separation by electrophoresis, and identifying body fluid-specific genes present in the sample as either a single or a mixed stain.

The total RNA is extracted with a denaturing solution, such as, guanidine isothiocyanate-phenol:chloroform. Then, the extracted total RNA is precipitated with an organic solvent, such as, isopropanol. A preferred enzyme, such as, deoxyribonuclease I (DNase I) is used to treat the extracted total RNA.

The preferred multiplex assay is an octaplex composed of eight body fluid-specific genes optimized for the detection of body fluids from four specific body tissues. The fluids, selected from four specific body tissues, are identified as, blood, saliva, semen and vaginal secretions.

The gene-specific primers are labeled with fluorescent dyes and are incorporated into a single multiplexed polymerase chain reaction (PCR) and the cDNA is amplified prior to separation according to size. A preferred method of separation is via capillary electrophoresis. The separated PCR product is then subjected to laser induced fluorescence for identification of body fluid-specific genes present in a sample stain.

Eight body fluid-specific genes are used in a multiplex, parallel assay and the eight body fluid-specific genes are selected from the group consisting of: beta-spectrin (SPTB), porphobilinogen deaminase (PBGD), the erythoid-specific variant known as variant 2, statherin (STATH), bistatin 3 (HTN3), protamine 1 (PRM1), protamine 2 (PRM2), mucin 4 (MUC4) and human beta-defensin 1 (HBD1).

The messenger RNA genes for human blood are identified as beta-spectrin (SPTB) and porphobilinogen deaminase (PBGD). The messenger RNA genes for vaginal secretions are identified as mucin 4 (MUC4) and human beta-defensin 1 (HBD1).

A kit is provided for use in preparing a multiplex, parallel assay to identify the source of at least four body fluids from a human being, comprising PCR primers pre-selected from 4 or more of the group consisting of 8 body fluid-specific gene primers constructed from SPTB, PBGD, STATH, HTN3, PRM1, PRM2, MUC4, and HBD-1 genes. In the kits, PCR primers are tagged with fluorescent dyes. It is possible to redesign primers for one or more of the body fluid-specific genes and it is understood that the redesigned primers are within the scope of the present invention.

Further objects and advantages of this invention will be apparent from the following detailed description and example of a presently preferred embodiment.

BRIEF DESCRIPTION OF THE DRAWING

FIG. 1 shows the sequences of the PCR primers for the various body fluid specific genes used in the assay.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

The invention provides a multiplex, parallel assay to identify the tissue source for at least four body fluids from a human being. The first step in the development of the invention is the identification of tissue-specific genes that are expressed in only one tissue. For example, each tissue type is comprised of cells that have a unique transcriptome, or gene expression profile, also known as the messenger ribonucleic acid (mRNA). The collection of genes that are expressed within the constellation of differentiated cells that make up a body fluid is called the multicellular transcriptome. These genes comprise ubiquitously expressed housekeeping genes, which are responsible for cell maintenance functions, and genes that are specifically expressed in certain tissues only.

The mRNA molecules are present in different quantities depending on the particular species of mRNA and the cell type, and can be classified as abundant, moderately abundant and rare. Although the present invention is dependent on the identification of tissue-specific mRNA molecules, it is not to be considered a limitation of the invention. As previously discussed, tissue-specific genes are still in the process of being identified.

In addition to identifying two body fluid-specific genes for each of four body fluids, the present invention provides a body fluid identification system or method. A number of design factors and assay quality controls ensure that the tissue-specific RT-PCR assays disclosed herein detect mRNA and not genomic DNA.

The two body fluid-specific genes for each of four body fluids that are the subject of the present invention, are identified in Table I below.

TABLE I

| BODY FLUID-SPECIFIC GENE: | BODY FLUIDS |
|---|---|
| beta-spectrin (SPTB) | BLOOD |
| porphobilinogen deaminase (PBGD) | BLOOD |
| statherin (STATH) | SALIVA |
| histatin 3 (HTN3) | SALIVA |
| protamine 1 (PRM1) | SEMEN |
| protamine 2 (PRM2) | SEMEN |
| mucin 4 (MUC4) | VAGINAL SECRETIONS |
| human beta-defensin 1 (HBD1) | VAGINAL SECRETIONS |

Fluorescent dye-labeled primers for the eight genes identified above, are incorporated into a single, multiplexed polymerase chain reaction (PCR). Following amplification, the PCR product is separated according to size with capillary electrophoresis and detected using laser induced fluorescence. The resulting profile, or collection of specific peaks on the electropherogram that represent the body fluid-specific genes, identify the body fluids that are present in the sample as a single or mixed stain. For this invention, the body fluids include, but are not limited to, blood, saliva, semen or vaginal secretions.

The following example provides further explanation of the present invention.

EXAMPLE

A physiological stain is prepared by collecting human blood via venipuncture; collecting 50 microliter (μl) aliquots placed onto cotton gauze and dried at room temperature. Freshly ejaculated semen is collected in plastic cups, and allowed to dry onto cotton swabs at room temperature. Buccal scrapings and saliva samples were obtained on cotton swabs, and dried at room temperature. Vaginal secretions, such as menstrual blood, are also obtained and dried at room temperature. For RNA or DNA isolation a 50 microliter (μl) blood or saliva stain, or a single semen, vaginal secretion, or menses blood stained cotton swab is used.

For RNA isolation, total RNA is extracted from blood, saliva, vaginal and semen stains with a denaturing solution, such as, guanidine isothiocyanate-phenol:chloroform and precipitated with isopropanol. Next, the extracted total RNA is treated with an enzyme, deoxyribonuclease I (DNase I), and then reverse-transcribed using random decamers as the first strand primer, producing complementary DNA (cDNA). Finally, the cDNA is amplified using gene-specific primers. The RT-PCR amplimer sizes are carefully chosen to span the range of approximately 100 base pairs to approximately 300 base pairs, wherein base pairs is the size of amplified product, to allow facile separation by standard electrophoresis on agarose gels or by capillary electrophoresis.

The primers are custom synthesized commercially. Primers for PBGD, PRM1, and PRM2 are described by A. N. Gubin and J. L. Miller, in "Human erythroid porphobilinogen deaminase exists in 2 splice variants." *Blood,* 97 (2001) pages 815-817, and K. Steger, K. Pauls, T. Klonisch, F. E. Franke and M. Bergmann, "Expression of Protamine-1 and -2 mRNA during human spermiogenesis." *Mol. Hum. Reprod.* 6 (2000) 219-225. The primer sequences (and expected product sizes) are shown in FIG. 1. The assay of the present invention, includes, but is not limited to, the primer sequences listed herein. A person skilled in the art will readily recognize that it is possible to redesign primers for one or more of the genes and it is understood that the redesigned primers are within the scope of the present invention.

The multiplex PCR reaction mixture contains buffer (10 mM Tris-HCl, pH 8.3, 50 mM KCl), 3.5 mM $MgCl_2$, 0.125 mM each dNTP, 5.48 µM PCR primers (see above), and 1.25 units of DNA Polymerase. The PCR primer pairs are added in the following concentrations: SPTB, 0.8 µM; PBGD, 0.24 µM; STATH, 0.4 µM; HTN3, 0.4 µM; PRM1, 0.04 µM; PRM2, 0.4 µM; HBD-1, 1.6 µM; MUC4, 1.6 µM. The standard PCR conditions used for the multiplex consists of a denaturing step (95° C., 11 min) followed by 35 cycles (94° C., 20 sec; 55° C., 30 sec; 72° C., 40 sec) and a final extension step (72° C., 5 min) using a thermocycler instrument.

Based on the above extraction and separation techniques, a multiplex RT-PCR assay is developed for the definitive identification of all of the body fluids commonly encountered in forensic casework analysis, namely blood, saliva, semen and vaginal secretions. The octaplex is composed of eight body fluid-specific genes and has been optimized for the detection of blood, saliva, semen, and vaginal secretions as single or mixed stains. The methodology is based on gene expression profiling analysis in which the body fluid-specific genes are identified by detecting the presence of appropriate mRNA species. The gene-specific primers are labeled with fluorescent dyes (such as Tet or Hex or Fam as indicated in FIG. 1) incorporated into a single multiplexed polymerase chain reaction (PCR). The cDNA is amplified using PCR, and the PCR product is separated according to size using a capillary electrohoresis instrument, and detected using laser induced fluorescence. The resulting profile identifies those body fluids present in a single or mixed stain.

Advantages of the mRNA-based approach, compared to conventional biochemical analysis include, but are not limited to, greater specificity, simultaneous and semi-automated analysis through a common assay format, improved timeliness, decreased sample consumption and compatibility with DNA extraction methodologies.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method for preparing a multiplex, parallel assay to identify the source of body fluids from a human being selected from the group consisting of one or more of blood, saliva, semen and vaginal secretions, comprising the steps of:
   a) obtaining a sample stain consisting of a single body fluid or multiple fluids from a human being;
   b) extracting total ribonucleic acid (RNA) from the sample stain;
   c) treating the total RNA with an enzyme;
   d) initiating a reverse-transcriptase (RT) reaction by treating total RNA with random decamers to produce cDNA;
   e) amplifying said cDNA using gene-specific primer pairs for each of the genes SPTB, PBGD, STATH, HTN3, PRM1, PRM2, MUC4, and HBD-1, wherein each gene is related to a specific human body fluid; SPTB and PBGD being genes specific for blood; STATH and HTN3 being genes specific for saliva; PRM1 and PRM2 being genes specific for semen; and HBD-1 and MUC4 being genes specific for vaginal secretions;
   f) controlling the size of the amplified cDNA to allow separation by electrophoresis; and
   g) identifying the body fluid-specific genes present in the sample, wherein the presence of one or more of said body fluid specific genes identifies the source of the body fluid(s) in the sample.

2. The method of claim 1, wherein the total RNA is extracted with a denaturing solution.

3. The method of claim 2, wherein the solution is guanidine isothiocyanate-phenol:chloroform.

4. The method of claim 3, wherein the extracted total RNA is precipitated with an organic solvent.

5. The method or claim 4, wherein the organic solvent is isopropanol.

6. The method of claim 1, wherein the enzyme used to treat the extracted total RNA is deoxyribonuclease I (DNase I).

7. The method of claim 1, wherein the gene-specific primers in step c) are labeled with fluorescent dyes.

8. The method of claim 1 wherein the gene specific primers are selected from the group consisting of Sequence IDs 1, 2, 3, 4, 5, 6, 7, 8, 9, 10, 11, 12, 13, 14, 15, and 16.

9. The method of claim 7, wherein the gene specific primers are selected from the group consisting of Sequence IDs 1, 2, 3, 4, 5, 6, 7, 8, 9, 10, 11, 12, 13, 14, 15, and 16.

* * * * *

UNITED STATES PATENT AND TRADEMARK OFFICE
CERTIFICATE OF CORRECTION

| | | |
|---|---|---|
| PATENT NO. | : 7,270,983 B1 | Page 1 of 1 |
| APPLICATION NO. | : 11/050538 | |
| DATED | : September 18, 2007 | |
| INVENTOR(S) | : Jack Ballantyne | |

It is certified that error appears in the above-identified patent and that said Letters Patent is hereby corrected as shown below:

STATEMENT REGARDING FEDERALLY SPONSORED RESEARCH OR DEVELOPMENT

Col. 1, line 17-18 should read

This invention was funded in part by U.S. ARMY, contract number DAAD0503C0047. The government has certain rights in this invention.

Signed and Sealed this

Seventeenth Day of May, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,270,983 B1 | Page 1 of 1 |
| APPLICATION NO. | : 11/050538 | |
| DATED | : September 18, 2007 | |
| INVENTOR(S) | : Jack Ballantyne | |

It is certified that error appears in the above-identified patent and that said Letters Patent is hereby corrected as shown below:

Column 1, line 6, below Title, insert:

--STATEMENT REGARDING FEDERALLY SPONSORED RESEARCH OR DEVELOPMENT

This invention was funded in part by U.S. ARMY, contract number DAAD0503C0047. The government has certain rights in this invention.--

This certificate supersedes the Certificate of Correction issued May 17, 2011.

Signed and Sealed this
Third Day of July, 2012

David J. Kappos
*Director of the United States Patent and Trademark Office*

UNITED STATES PATENT AND TRADEMARK OFFICE
CERTIFICATE OF CORRECTION

PATENT NO.         : 7,270,983 B1                                               Page 1 of 1
APPLICATION NO.    : 11/050538
DATED              : September 18, 2007
INVENTOR(S)        : Jack Ballantyne It is certified that error appears in the above-identified patent and that said Letters Patent is hereby corrected as shown below:

Column 1, lines 17-18

"STATEMENT REGARDING FEDERALLY SPONSORED RESEARCH OR DEVELOPMENT

This invention was funded in part by U.S. ARMY, contract number DAAD0503C0047. The government has certain rights in this invention." (as inserted in specification above heading "BACKGROUND AND PRIOR ART" by the Certificates of Correction issued May 17, 2011 and July 3, 2012) is to be deleted.

Signed and Sealed this
First Day of January, 2013

David J. Kappos
*Director of the United States Patent and Trademark Office*